United States Patent
Chuang et al.

(10) Patent No.: US 9,080,991 B2
(45) Date of Patent: Jul. 14, 2015

(54) ILLUMINATING A SPECIMEN FOR METROLOGY OR INSPECTION

(75) Inventors: Yung-Ho (Alex) Chuang, Cupertino, CA (US); Vladimir Levinski, Nazareth-Ilit (IL); Xuefeng Liu, San Jose, CA (US); John Fielden, Los Altos, CA (US)

(73) Assignee: KLA-Tencor Corp., Milpitas, CA (US)

( * ) Notice: Subject to any disclaimer, the term of this patent is extended or adjusted under 35 U.S.C. 154(b) by 1109 days.

(21) Appl. No.: 13/073,986

(22) Filed: Mar. 28, 2011

(65) Prior Publication Data

US 2011/0228263 A1    Sep. 22, 2011

Related U.S. Application Data

(63) Continuation-in-part of application No. 13/061,936, filed as application No. PCT/US2009/058819 on Sep. 29, 2009.

(60) Provisional application No. 61/100,990, filed on Sep. 29, 2008.

(51) Int. Cl.
*G01N 21/00* (2006.01)
*G01N 21/95* (2006.01)
*G01N 21/47* (2006.01)

(52) U.S. Cl.
CPC ...... *G01N 21/9501* (2013.01); *G01N 2021/479* (2013.01)

(58) Field of Classification Search
CPC .................. G01N 15/0205; G01N 15/1459
USPC ........................................... 356/237.1–237.5
See application file for complete search history.

(56) References Cited

U.S. PATENT DOCUMENTS

| 4,999,014 A | 3/1991 | Gold et al. |
| 5,042,951 A | 8/1991 | Gold et al. |

(Continued)

FOREIGN PATENT DOCUMENTS

| JP | 2001-274081 | 10/2001 |
| JP | 2004-110072 | 4/2004 |
| WO | 2010/037106 | 4/2010 |

OTHER PUBLICATIONS

International Search Report and Written Opinion for PCT/US2012/023205 mailed Nov. 23, 2012.
Chuang et al. "Laser-beam pulse shaping using dispersive spectral filtering" SPIE, Bellingham, WA, 1993, vol. 1870, pp. 34-46.

(Continued)

*Primary Examiner* — Kara E Geisel
*Assistant Examiner* — Iyabo S Alli
(74) *Attorney, Agent, or Firm* — Ann Marie Mewherter

(57) ABSTRACT

Illumination subsystems of a metrology or inspection system, metrology systems, inspection systems, and methods for illuminating a specimen for metrology measurements or for inspection are provided. One illumination subsystem includes a light source configured to generate coherent pulses of light and a dispersive element positioned in the path of the coherent pulses of light, which is configured to reduce coherence of the pulses of light by mixing spatial and temporal characteristics of light distribution in the pulses of light. The illumination subsystem also includes an electro-optic modulator positioned in the path of the pulses of light exiting the dispersive element and which is configured to reduce the coherence of the pulses of light by temporally modulating the light distribution in the pulses of light. The illumination subsystem is configured to direct the pulses of light from the electro-optic modulator to a specimen.

27 Claims, 6 Drawing Sheets

(56) References Cited

U.S. PATENT DOCUMENTS

| | | | |
|---|---|---|---|
| 5,159,412 | A | 10/1992 | Willenborg et al. |
| 5,181,080 | A | 1/1993 | Fanton et al. |
| 5,453,871 | A | 9/1995 | Kolner et al. |
| 7,068,363 | B2 * | 6/2006 | Bevis et al. ................ 356/237.5 |
| 7,248,375 | B2 | 7/2007 | Opsal et al. |
| 7,423,818 | B2 | 9/2008 | Hemenway et al. |
| 7,436,503 | B1 | 10/2008 | Chen et al. |
| 7,667,841 | B2 | 2/2010 | Opsal |
| 2005/0128473 | A1 * | 6/2005 | Karpol et al. .............. 356/237.4 |
| 2005/0254049 | A1 | 11/2005 | Zhao et al. |
| 2007/0171407 | A1 * | 7/2007 | Cole et al. .................... 356/300 |
| 2009/0290156 | A1 | 11/2009 | Popescu et al. |

OTHER PUBLICATIONS

International Search Report and Written Opinion for PCT/US2009/058819 mailed Apr. 19, 2010.
International Preliminary Report on Patentability for PCT/US2009/058819 mailed Apr. 7, 2011.
Wilcox et al. Fusion Laser Oscillator and Pulse-forming System Using Integrated Optics, SPIE, Bellingham, WA, 1993, vol. 1870, pp. 53-63.
Notice of Reasons for Refusal for Japanese Patent Application No. 2011-529361 mailed Jul. 9, 2013.
International Preliminary Report on Patentability for PCT/US2012/023205 mailed Oct. 19, 2013.

* cited by examiner

ILLUMINATING A SPECIMEN FOR METROLOGY OR INSPECTION

PRIORITY CLAIM

This application is a continuation-in-part of U.S. patent application Ser. No. 13/061,936 filed Mar. 2, 2011, which is a National Stage application of International Application No. PCT/US09/58819 filed Sep. 29, 2009, which claims priority to U.S. Provisional Application No, 61/100,990 entitled "Speckle Reduction Approach for Pulsed Laser Light Source," filed Sep. 29, 2008, which is incorporated by reference as if fully set forth herein.

BACKGROUND OF THE INVENTION

1. Field of the Invention

The present invention generally relates to illuminating a specimen for inspection or metrology. Certain embodiments relate to reducing the coherence of pulses of light for inspection and metrology applications.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. Metrology and inspection processes are used at various steps during a semiconductor manufacturing process to monitor and control the process. Metrology processes are used to measure one or more characteristics of the wafers. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

Inspection processes are used to detect the presence of defects such as patterning defects and particles on the surface of wafers. For example, inspection processes can include imaging a region of a wafer at high magnification and then comparing that image, e.g., with 1) images of one or more other regions that are supposed to contain the same pattern or 2) a theoretical image, in order to detect differences in the image that may represent defects such as defects in the pattern and particles on, or embedded in, the surface of the wafer. A defect or particle that is smaller than the image resolution of the inspection system optics can often be detected by a change in the reflected or scattered light caused by that defect or particle. Typically, in an inspection process, it is desired to inspect a high percentage, or even 100%, of the wafer surface. Since each high magnification image covers only a small fraction of the wafer surface area, many such images have to be acquired in order to cover the total area that is to be inspected.

In general, metrology and inspection processes can take a relatively long time, particularly when the number of sites on the wafers at which measurements or inspections are performed is relatively large. One obstacle to reducing the time in which metrology and inspection processes can be performed is the substantial difficulty of reducing the time involved in moving the wafer and/or system optics such that multiple sites on the wafer can be measured or inspected. Therefore, one approach to decreasing the time involved in metrology and inspection processes involves continuously moving the wafer and/or system optics relative to one another during the metrology or inspection process. However, such an approach significantly reduces the amount of time in which the measurement can be performed or an image can be captured. Therefore, such an approach requires a light source that can produce a sufficient amount of light in a substantially short period of time. One such light source is a pulsed laser light source. Such light sources have a disadvantage in that the light has a speckle pattern due to the coherence of the light, which can interfere with the metrology measurements, degrade the quality of inspection images, or cause spurious intensity changes in those images. As such, a significant obstacle to using such a light source in a metrology or inspection system that performs measurements or inspection as the wafer and/or system optics are continuously moved relative to one another is that the speckle pattern must be suppressed relatively quickly, and particularly more quickly than the time in which the speckle pattern can be suppressed using mechanical devices, time averaging procedures, or other currently used methods for suppressing speckle patterns.

Accordingly, it would be advantageous to develop illumination methods and/or subsystems for metrology and inspection systems that can provide adequate light with a sufficiently suppressed speckle pattern in a substantially short amount of time.

SUMMARY OF THE INVENTION

The following description of various embodiments is not to be construed in any way as limiting the subject matter of the appended claims.

One embodiment relates to an inspection system. The inspection system includes an illumination subsystem. The illumination subsystem includes a light source configured to generate coherent pulses of light. The illumination subsystem also includes a dispersive element positioned in the path of the coherent pulses of light. The dispersive element is configured to reduce coherence of the pulses of light by mixing spatial and temporal characteristics of light distribution in the pulses of light. In addition, the illumination subsystem includes an electro-optic modulator positioned in the path of the pulses of light exiting the dispersive element. The electoroptic modulator is configured to reduce the coherence of the pulses of light by temporally modulating the light distribution in the pulses of light. The illumination subsystem is configured to direct the pulses of light from the electro-optic modulator to a specimen. The inspection system also includes a detection subsystem configured to detect light from the specimen and to generate output responsive to the detected light. In addition, the inspection system includes a processor configured to detect defects on the specimen using the output. The inspection system may be further configured according to any embodiments described herein.

An additional embodiment relates to a method for illuminating a specimen for inspection. The method includes generating coherent pulses of light. The method also includes reducing coherence of the pulses of light by mixing spatial and temporal characteristics of light distribution in the pulses of light. In addition, the method includes reducing the coherence of the pulses of light by temporally modulating the light distribution in the pulses of light. The method further includes subsequent to the reducing steps, directing the pulses of light to the specimen positioned in an inspection system.

Each of the steps of the method described above may be further performed as described herein. In addition, the method described above may include any other step(s) of any other method(s) described herein. Furthermore, the method described above may be performed by any of the subsystems and systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
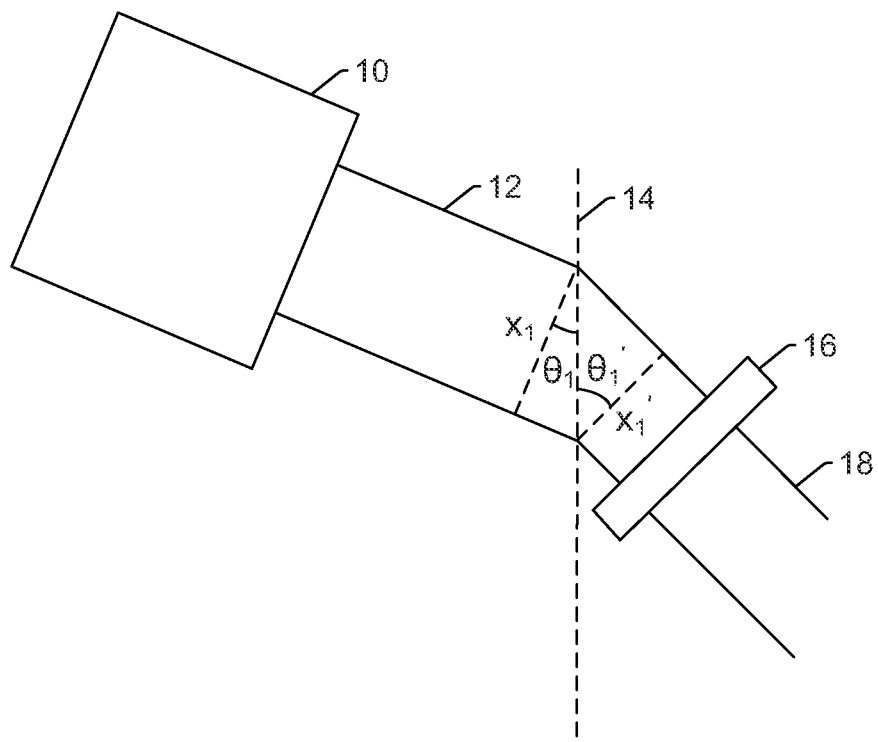
FIG. 1 is a schematic diagram illustrating a cross-sectional view of an embodiment of an illumination subsystem.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

In general, the embodiments described herein relate to speckle suppression approaches for pulsed laser light sources. For example, the embodiments described herein provide a solution for suppression of speckle patterns produced by a coherent pulsed light source (a pulsed laser). In some embodiments, the specimen may be a wafer such as that on which semiconductor devices are or can be fabricated. In addition, although some description is provided herein with respect to a wafer or wafers, it is to be understood that the embodiments described herein can be used to illuminate any other specimen for metrology measurements or inspection.

The market need for substantially increasing the number of measured or inspected sites on a wafer demands a significant reduction in the time required for measurement or inspection at each site. For example, recently used measurement sequences include navigation from one site to another, target acquisition, focus correction, and output acquisition (e.g., image or scatterometry signal grabbing). The navigation procedure in of itself includes accelerating and decelerating phases, which increase the navigation time by at least a factor of two. Owing to tight specifications for mechanical vibrations, these accelerating and decelerating phases prevent measurement time reduction to the time required for next node generations.

One embodiment relates to an illumination subsystem of a metrology or inspection system. In one embodiment, the metrology or inspection system is configured to cause continuous relative movement between the specimen and at least some optics of at least one of the illumination and detection subsystems described herein during metrology or inspection of the specimen performed by the metrology or inspection system. For example, the metrology or inspection system may be configured to cause continuous relative movement between the specimen and a detection subsystem of the system during measurements or inspection of the specimen performed by the system. The metrology or inspection system may be configured to cause such continuous relative movement as described further herein. For example, in order to provide the measuring time reductions required for next node generations, one approach is to perform the measurements "on the fly." This concept implies that the metrology or inspection system optics (e.g., the detection subsystem or optical sensor) and/or the wafer are continuously moved relative to one another and output acquisition (e.g., image grabbing or other signal grabbing) is performed using a light source such as a flash broadband light source or a pulsed laser.

The illumination subsystem includes a light source configured to generate coherent pulses of light. For example, as shown in FIG. 1, the illumination subsystem includes light source 10 configured to generate coherent pulses of light (shown generally in FIG. 1 by incoming beam 12 having cross-sectional dimension $X_1$). In one embodiment, a duration of the pulses of light generated by the light source is less than 10 nanoseconds. One main distinction between the embodiments described herein and other known means of speckle reduction such as a rotating diffuser, etc. is that the embodiments are applicable and mostly designed for relatively short pulses (e.g., a few nanoseconds) of illumination. In particular, as described further herein, the embodiments provide a new de-coherence approach for ultra short pulses of light. In one embodiment, the light source is a laser light source. For example, as described above, metrology measurements or inspection may be performed using a flash broadband light source or a pulsed laser. However, at this moment, only a pulsed laser light source can provide the required amount of light since the duration of the pulses of light is limited to a few nanoseconds. In particular, for a typical navigation velocity of about 1 m/sec, the maximum allowable shift over the target or measurement site during output acquisition is a few nanometers. The pulsed laser light source may include any suitable commercially available pulsed laser light source.

In another embodiment, the illumination subsystem is not configured to reduce the coherence of the pulses of light using mechanical devices. For example, a coherent light source produces a well-known speckle problem, the solution to which, in the case of the metrology and inspection systems described herein, becomes complicated due to the pulse duration of only a few nanoseconds. In particular, this pulse duration prevents the use of widespread approaches such as a rotating diffuser or other mechanical devices for speckle amplitude reduction. Indeed, common practice for speckle suppression is using a time averaging procedure where during the integration (image/signal grabbing) time many different speckle configurations are summed or averaged. Since the amplitude of speckle is reduced as a square root of the number of realizations, about $10^4$ different speckle configurations need to be summed or averaged in order to reduce the speckle amplitudes to the allowable for metrology and inspection application signal-to-noise ratios. Accordingly, for pulses having a duration of a few nanoseconds, less than a picosecond time interval is needed for each speckle realization, which cannot be achieved using mechanical devices. Therefore, a significant advantage of the embodiments described herein is that they provide a speckle suppression mechanism having approximately the same efficiency as a rotating diffuser but for a time scale that is smaller by 4-6 orders of magnitude, which makes possible using pulsed coherent light sources for metrology and inspection applications. In addition, the embodiments described herein have significant value because they make possible using existing pulsed laser light sources for "on the fly" metrology and inspection applications.

A tenth picosecond time interval for the visible light spectrum is equivalent to a few nanometers spectral width. The main idea of the embodiments described herein is to make use of the spectral range finiteness in order to perform a substantially quick temporal modulation of the light beam, which can be changed on the required tenth picosecond time intervals, and transform the temporal modulation to spatial modulation. The use of a dispersive element and an electro-optic modulator is the core of the new approaches described herein for speckle reduction. For example, the illumination subsystem includes a dispersive element positioned in the path of the coherent pulses of light. As shown in FIG. 1, the dispersive element can be positioned at plane 14 arranged at angle $\theta_1$ to the cross-section of the coherent pulses of light. As further shown in FIG. 1, the pulses of light exit the dispersive element at angle $\theta_1'$ and with cross-sectional dimension $X_1'$. In one embodiment, the dispersive element is a prism. In another embodiment, the dispersive element is a diffraction grating. The dispersive element is configured to reduce coherence of the pulses of light by mixing spatial and temporal characteristics of light distribution in the pulses of light. In particular, a dispersive element such as a prism or diffraction grating provides some mixing between spatial and temporal characteristics of the light distribution in the pulses of light. For example, a diffraction grating transforms a separate dependence of the light distribution in the pulses of light on spatial and temporal coordinates to a dependence of the light distribution on mixed spatial-temporal coordinates:

$$E(t,x) \Rightarrow E(t-\beta x, x).$$

The dispersive element may include any suitable prism or diffraction grating, which may vary depending on the optical characteristics of the illumination subsystem and the metrology or inspection system.

The illumination subsystem further includes an electro-optic modulator positioned in the path of the pulses of light exiting the dispersive element. For example, as shown in FIG. 1, the illumination subsystem may include electro-optic modulator 16 positioned in the path of the pulses of light exiting the dispersive element. The electro-optic modulator is configured to reduce the coherence of the pulses of light by temporally modulating the light distribution in the pulses of light. In particular, the electro-optic modulator provides an arbitrary temporal modulation of the light distribution. Therefore, the dispersive element and the electro-optic modulator have a combined effect on the pulses of light generated by the light source. In particular, the combination of the dispersive element with the electro-optic modulator creates an arbitrary temporal modulation and transforms the temporal modulation to an arbitrary spatial modulation.

Figure 2:
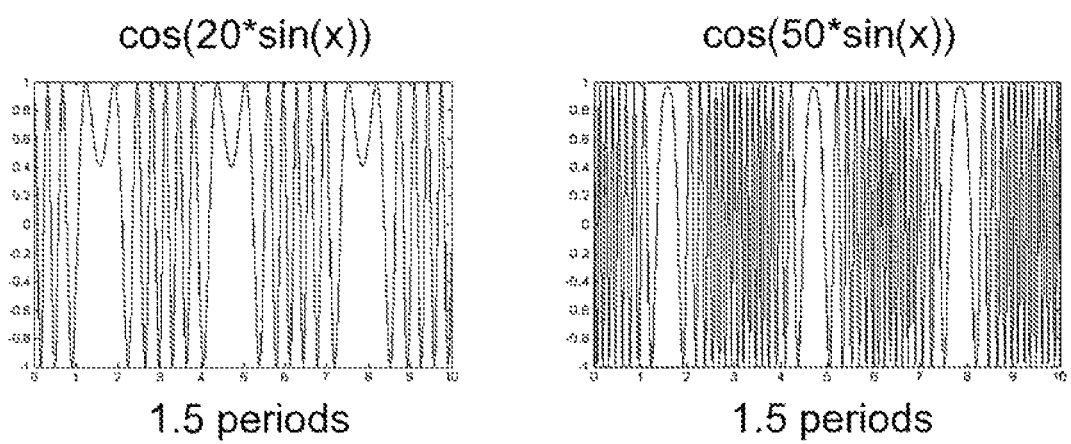
FIG. 2 includes plots illustrating how increasing the amplitude of an electro-optic modulator included in an embodiment of an illumination subsystem described herein can reduce de-coherence time.

In one embodiment, the electro-optic modulator is configured to change the temporal modulation of the light distribution in the pulses of light at tenth picosecond time intervals. In another embodiment, the electro-optic modulator is configured to provide about $10^3$ aperiodic samples on each period thereby providing a de-coherence time of about $10^{-13}$ seconds. For example, an electro-optic modulator introduces the following time varying phasor, $\exp(i\phi_m \sin(\omega_m t))$, where $\omega_m \sim 10^9\text{-}10^{10}$ Hz is the modulation frequency, $$\phi_m = \frac{2\pi}{\lambda} \Delta n \cdot l,$$

l is the thickness of the electro-optic modulator, $\lambda$ is the wavelength, and $\Delta n \sim 10^{-3}$ is the amplitude of the change of the refractive index. An electro-optic modulator with a frequency of $\sim 10^9\text{-}10^{10}$ Hz provides the minimal de-coherence time $\tau_D \sim 10^{-10}$ which is 3 orders of magnitude larger than the required tenth picosecond time. However, a relatively high amplitude ($\phi_m \sim 10^3$) may provide $\sim 10^3$ aperiodic samples on each period and in this manner may reduce the de-coherence time to a desirable $\tau_D \sim 10^{-13}$ seconds. Examples of plots illustrating how increasing the amplitude of the electro-optic modulator can reduce de-coherence time are shown in FIG. 2.

In some embodiments, the electro-optic modulator is configured to operate in a traveling wave operation mode. For example, using an electro-optic modulator of $10^5 \lambda \sim 5$ cm length provides a speckle suppression mechanism of approximately the same efficiency as a rotating diffuser but for a time scale about 4-6 orders smaller. However, if the electro-optic modulator length is about 5 cm, the time (T) of a pulse passing through the electro-optic modulator is $T \sim 2*10^{-10}$ seconds which is about the period of modulator oscillations. Accordingly, the effect of the electro-optic modulator may be described as:

$$\exp\left[i\frac{\phi_m}{T}\int_t^{t+T} dt \sin(\omega_m t)\right] = \exp\left[i\phi_m \cdot \text{sinc}\left(\frac{T\omega_m}{2}\right) \cdot \sin(\omega_m t)\right]$$

For example, for $T \sim 10^{-10}$ seconds, a reduction of modulator amplitude by an order of magnitude can be obtained. To solve this problem, electro-optic modulator working in a traveling wave operation mode may be provided or an electro-optic modulator with a better dynamic range of refraction index variability can be used. Traveling wave mode electro-optic modulators are generally known in the art and as such will not be discussed further herein. The electro-optic modulator may include any suitable commercially available electro-optic modulator and can be selected based on the characteristics of the electro-optic modulator, the illumination subsystem, and the metrology or inspection system described herein.

The illumination subsystem is configured to direct the pulses of light from the electro-optic modulator to a specimen positioned in the metrology or inspection system. For example, the illumination subsystem may be configured to direct pulses of light (shown in FIG. 1 generally by light beam 18) to a specimen as further described herein.

Figure 3:
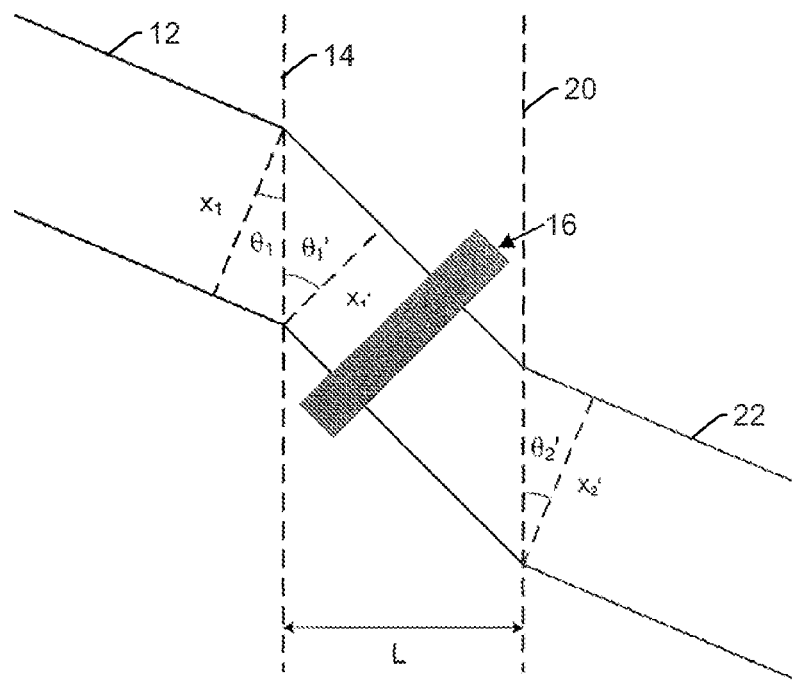
FIGS. 3-8 are schematic diagrams illustrating cross-sectional views of a portion of various embodiments of an illumination subsystem.

In one embodiment, the illumination subsystem includes an additional dispersive element positioned in the path of the pulses of light exiting the electro-optic modulator. For example, as shown in FIG. 3, the illumination subsystem may include an additional dispersive element positioned in plane 20 in the path of the pulses of light exiting electro-optic modulator 16. The additional dispersive element is configured to reduce the coherence of the pulses of light by mixing the spatial and temporal characteristics of the light distribution in the pulses of light. In this manner, the arbitrary temporal modulation of the light by the electro-optic modulator can be transformed to an arbitrary spatial modulation by performing a reverse light beam transformation using a dispersive element that is similar to the first dispersive element. As such, FIG. 3 illustrates a spatial light distribution modulator.

Figure 4:
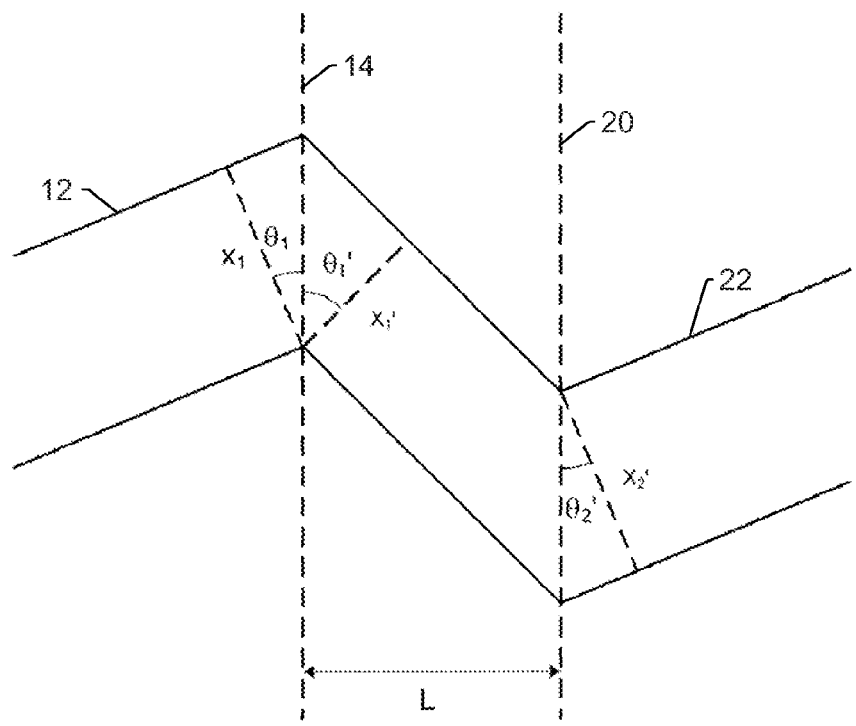

As shown in FIG. 3, the planes in which the two dispersive elements are positioned may be spaced apart by a distance, L. In addition, the pulses of light (shown generally in FIG. 3 by outgoing beam 22) may exit the additional dispersive element at an angle $\theta_2'$, between the cross-section of the pulses of light and plane 20, and with cross-sectional dimension $X_2'$. However, the angles shown in FIG. 3 (between the cross-sections of the pulses of light entering and exiting the dispersive elements and the planes in which the dispersive elements are positioned) are not limiting. For example, as shown in FIG. 4, the angles (between the cross-sections of the pulses of light entering and exiting the dispersive elements and the planes in which the dispersive elements are positioned) may be different from those shown in FIG. 3 and may vary depending on the characteristics of the dispersive elements (e.g., the diffraction by the gratings). The portions of the illumination subsystems shown in FIGS. 3 and 4 may be further configured as described herein. The additional dispersive element may be further configured as described herein with respect to the other dispersive element.

In some embodiments, the illumination subsystem is configured to direct the pulses of light from the additional dispersive element to the specimen. In this manner, the illumination subsystem is effectively configured to direct the pulses of light from the electro-optic modulator to the specimen. The illumination subsystem may be configured in this manner as described further herein.

Figure 5:
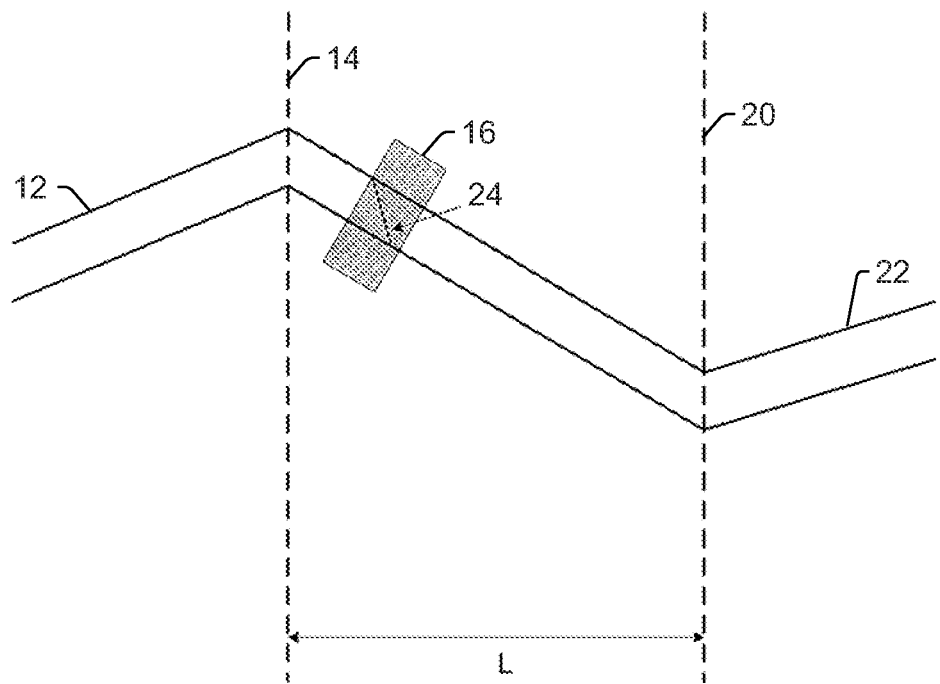

As shown in FIG. 5, wavefront 24 of the pulses of light exiting the dispersive element may be arranged at an angle with respect to the plane of electro-optic modulator 16. In this manner, different parts of the original wavefront of the pulses of light are modulated with different phases as the pulses of light propagate through the electro-optic modulator. If the electro-optic modulator is positioned immediately after the dispersive element (e.g., the first grating), the output wave becomes:

$$E_{E0}(t,x)=E(t-\beta x,x)\exp(i\phi_m \sin(\omega_m t)).$$

After the second dispersive element (e.g., the second grating), the output wave becomes:

$$\exp(i\phi_m \sin(\omega_m t)) \Rightarrow \exp\{i\phi_m \sin[\omega_m(t-\alpha x)]\}$$

In this manner, the additional dispersive element the second grating) transforms the temporal modulation to the spatial modulation. The portion of the illumination subsystem shown in FIG. 5 may be further configured as described herein.

Figure 6:
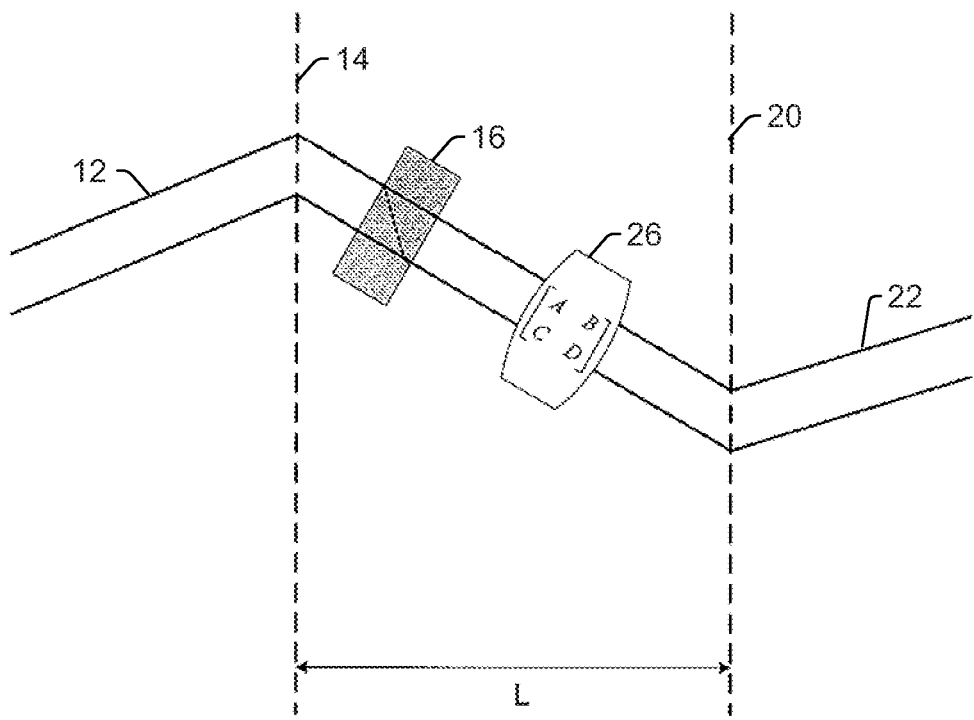

In another embodiment, the illumination subsystem includes refractive optics positioned between the electro-optic modulator and the additional dispersive element. For example, in order to enhance the effect of the spatial modulation, the length of the optical path may be increased using additional optics positioned between the electro-optic modulator and the additional dispersive element (e.g., the second grating). In one such example, as shown in FIG. 6, the illumination subsystem may include refractive optics 26 positioned between the electro-optic modulator and the additional dispersive element. Refractive optics 26 may include any suitable lens system that enables the modulation of the (effective) diffraction length L and control of beam size. The portion of the illumination subsystem shown in FIG. 6 may be further configured as described herein.

Figure 7:
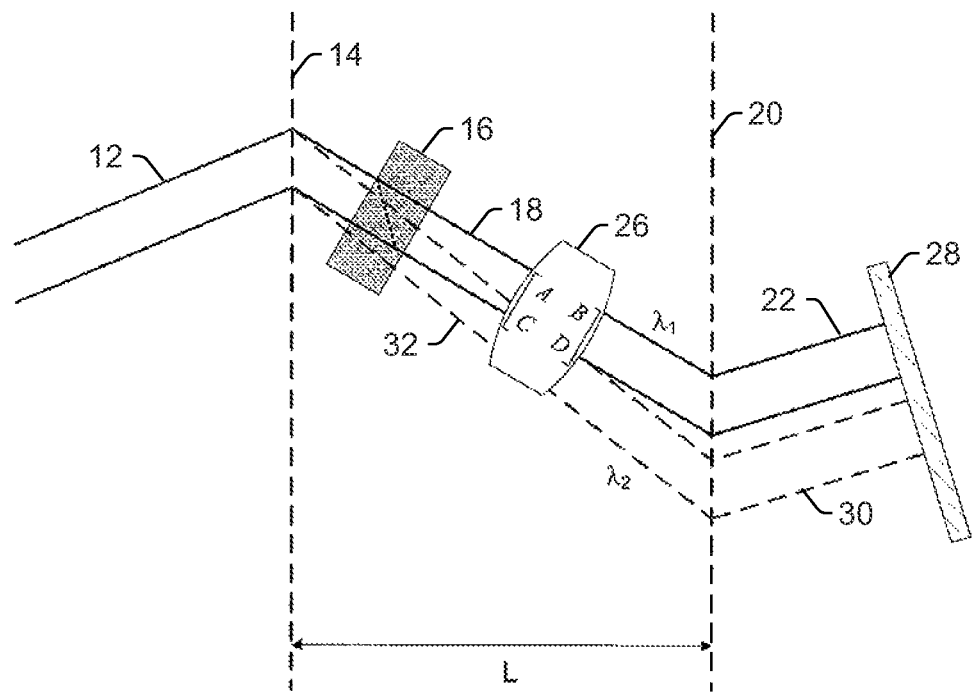

To make more efficient use of the electro-optic modulator, a reflective element may be positioned at the end of the spatial light distribution modulation subsystem. For example, in an additional embodiment, the illumination subsystem includes a reflective element positioned in the path of the pulses of light exiting the additional dispersive element. The reflective element is configured to direct the pulses of light exiting the additional dispersive element back through the additional dispersive element, the electro-optic modulator, and the dispersive element. For example, as shown in FIG. 7, the illumination subsystem may include reflective element 28 positioned in the path of the pulses of light (shown generally by light beam 22) exiting the additional dispersive element positioned in plane 20. Reflective element 28 is configured to direct the pulses of light (shown generally by light beam 22) exiting the additional dispersive element back through the additional dispersive element, electro-optic modulator 16, and the dispersive element positioned in plane 14. As further shown in FIG. 7, if the illumination subsystem includes refractive optics 26, the pulses of light reflected by the reflective element may also pass back through the refractive optics. The reflective element may include any suitable reflective element such as a mirror. In this manner, the arbitrary temporal modulation of the light distribution performed by the electro-optic modulator can be transformed to an arbitrary spatial modulation by reversing the direction of the pulses of light so that they pass through the same dispersive elements on their way back along the reversed direction. As such, the illumination subsystem may perform modulation twice using the electro-optic modulator (first on the incoming beam of the pulses of light and then on the reflected beam of the pulses of light).

In such an embodiment, the illumination subsystem is configured to direct the pulses of light from the dispersive element to the specimen. In this manner, the illumination subsystem is effectively configured to direct the pulses of light from the electro-optic modulator to the specimen. The illumination subsystem may be configured to direct the pulses of light from the dispersive element to the specimen as described further herein. The portion of the illumination subsystem shown in FIG. 7 may be further configured as described herein.

In some embodiments, the pulses of light generated by the light source include light having different wavelengths. For example, the light source may include a multi-wavelength pulsed laser light source configured to generate pulses of light having two or more wavelengths (e.g., $\lambda_1$, $\lambda_2$, etc.). In one such embodiment, the illumination subsystem is configured to direct the light having the different wavelengths along different optical paths through the illumination subsystem. For example, the illumination subsystem may be configured to have the bandwidth effect shown in FIG. 7. In particular, different wavelengths may travel through different optical paths. In the example shown in FIG. 7, pulses of light having a first wavelength (e.g., $\lambda_1$) may travel back along the optical path shown generally by light beams 22 and 18 contrast, pulses of light having a second, different wavelength (e.g., $\lambda_2$) may travel back along an optical path shown generally by light beams 30 and 32. In such a configuration, the optical path lengths for the different wavelengths will be different. For example, as shown in FIG. 7, the optical path length may be longer for the pulses of light having wavelength $\lambda_2$. As such, after reflection by reflective element 28, pulses of light having different wavelengths may be separated in time, which then enables temporal modulation.

Figure 8:
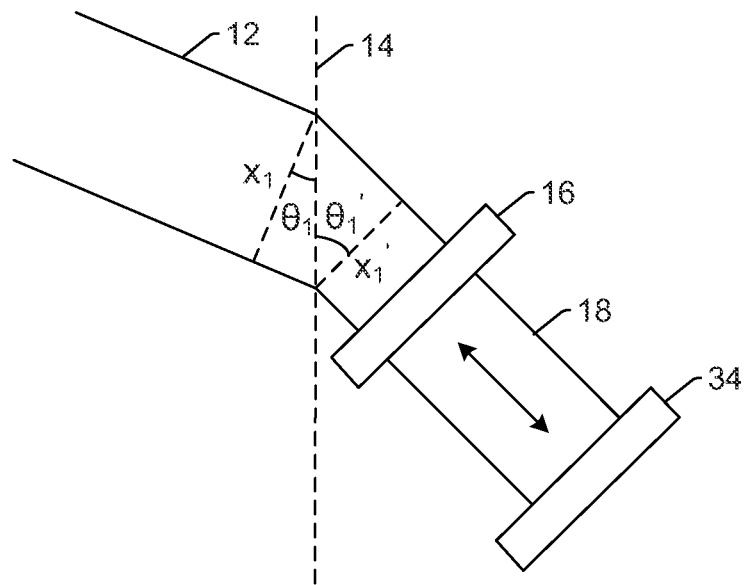

The concept of reflecting the pulses of light back through the optics of the illumination subsystem may be used regardless of whether the illumination subsystem includes one or two dispersive elements. For example, in another embodiment, the illumination subsystem includes a reflective element positioned in the path of the pulses of light exiting the electro-optic modulator. In one such embodiment, as shown in FIG. 8, the illumination subsystem may include reflective element 34 positioned in the path of the pulses of light (shown generally in FIG. 8 by light beam 18) exiting electro-optic modulator 16. The reflective element is configured to direct the pulses of light exiting the electro-optic modulator back through the electro-optic modulator and the dispersive element. For example, reflective element 34 may be configured to direct the pulses of light exiting electro-optic modulator 16 back through the electro-optic modulator and the dispersive element positioned at plane 14. In this manner, the arbitrary temporal modulation of the light distribution performed by the electro-optic modulator can be transformed to an arbitrary spatial modulation by reversing the direction of the pulses of light so that they pass through the same dispersive element on their way back along the reversed direction. Reflective element 34 may include any suitable reflective element such as a mirror.

In such an embodiment, the illumination subsystem is configured to direct the pulses of light from the dispersive element to the specimen. In this manner, the illumination subsystem is effectively configured to direct the pulses of light from the electro-optic modulator to the specimen. The illumination subsystem may be configured to direct the pulses of light from the dispersive element to the specimen as described further herein. The portion of the illumination subsystem shown in FIG. 8 may be further configured as described herein.

Each of the embodiments of the illumination subsystem described above may be further configured as described herein. In addition, each of the embodiments of the illumination subsystem described above may be included in any of the metrology and inspection systems described herein. Furthermore, each of the embodiments of the illumination subsystem described above may be used to perform any of the methods described herein.

Figure 9:
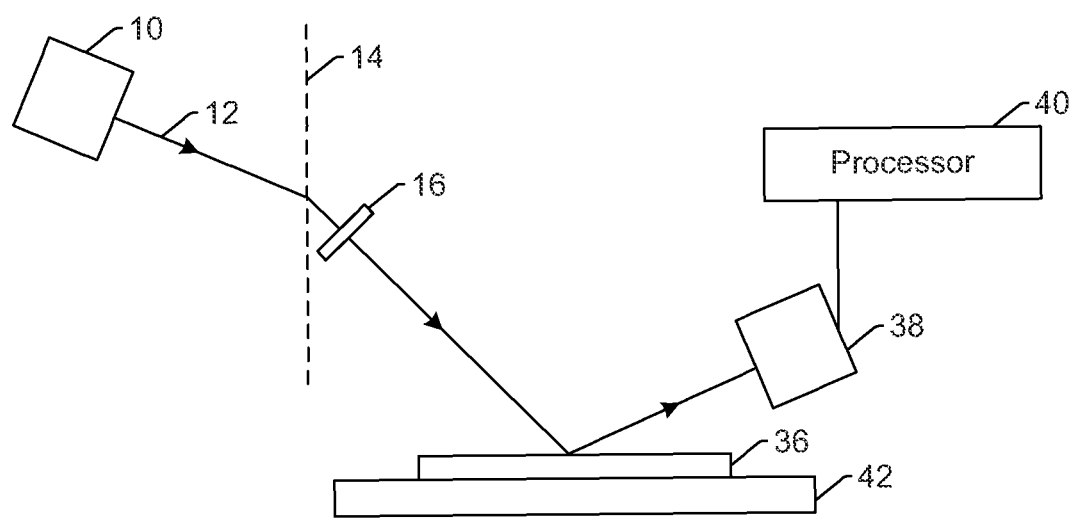
FIGS. 9-10 are schematic diagrams illustrating side views of various embodiments of a metrology system.

Another embodiment relates to a metrology system. FIG. 9 illustrates one example of such a metrology system. The metrology system includes an illumination subsystem. As shown in FIG. 9, the illumination subsystem includes light source 10 configured to generate coherent pulses of light (shown generally in FIG. 9 by light beam 12). The light source may be further configured as described herein. The illumination subsystem also includes a dispersive element positioned in the path of the coherent pulses of light. As shown in FIG. 9, the dispersive element may be positioned in plane 14 in the path of the coherent pulses of light. The dispersive element is configured to reduce coherence of the pulses of light by mixing spatial and temporal characteristics of light distribution in the pulses of light. The dispersive element may be further configured as described herein. As further shown in FIG. 9, the illumination subsystem includes electro-optic modulator 16 positioned in the path of the pulses of light exiting the dispersive element. The electro-optic modulator is configured to reduce the coherence of the pulses of light by temporally modulating the light distribution in the pulses of light. The electro-optic modulator may be further configured as described herein.

The illumination subsystem is configured to direct the pulses of light from the electro-optic modulator to specimen 36 positioned in the metrology system. For example, as shown in FIG. 9, the elements of the illumination subsystem may be arranged such that the pulses of light exiting the electro-optic modulator are directed to the specimen at an oblique angle of incidence without passing through any additional optical elements. However, the illumination subsystem may include one or more additional refractive and/or reflective optical elements (not shown) that are configured to direct the light exiting the electro-optic modulator to the specimen at an oblique angle of incidence. The one or more additional refractive and/or reflective optical elements may include, for example, focusing lenses, flat mirrors, and the like. In addition, the illumination subsystem may be configured to direct the light exiting the electro-optic modulator to the specimen at any suitable oblique angle of incidence or a normal angle of incidence. Furthermore, the metrology system may include a control subsystem (not shown) that is configured to alter one or more parameters of the illumination subsystem (e.g., such as a position of one or more of the elements of the illumination subsystem) such that the light can be directed from the electro-optic modulator to the specimen at different angles of incidence.

The metrology system also includes a detection subsystem configured to detect light from the specimen and to generate output responsive to the detected light. For example, as shown in FIG. 9, the detection subsystem may include detector 38. The detector may include any suitable detector such as an imaging detector or a non-imaging detector. In addition, the detection subsystem may include any additional optical elements (not shown, e.g., one or more optical elements configured to collect the light from the specimen, to focus the light collected from the specimen to the detector, or to change the path of the light from the specimen such that it can be directed to the detector). The detection subsystem may be configured to detect light propagating at any suitable angle from the specimen, which may vary depending on the measurements of the specimen being performed by the metrology system. For example, the detector and any additional optical elements included in the detection subsystem may be configured to detect light reflected, scattered, or diffracted from the specimen. The measurements of the specimen being performed by the metrology system may include any suitable measurements such as scatterometry measurements, ellipsometry measurements, and reflectometry measurements.

In addition, the metrology system includes a processor configured to determine one or more characteristics of the specimen using the output. For example, as shown in FIG. 9, the metrology system may include processor 40. The processor may be configured to determine the one or more characteristics of the specimen using the output in any suitable manner. The one or more characteristics of the specimen that are determined by the processor may vary depending on the specimen and the measurements performed by the metrology system. For example, the one or more characteristics of the specimen that are determined by the processor may include a thin film thickness, a dimension of a patterned structure formed on the specimen, roughness of a film formed on the specimen, roughness of a patterned structure formed on the specimen, and overlay (or the position of patterned structures formed on one layer of the specimen with respect to the position of patterned structures formed on another layer of the specimen).

Processor 40 may be included in any suitable computer system. The computer system may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Figure 10:
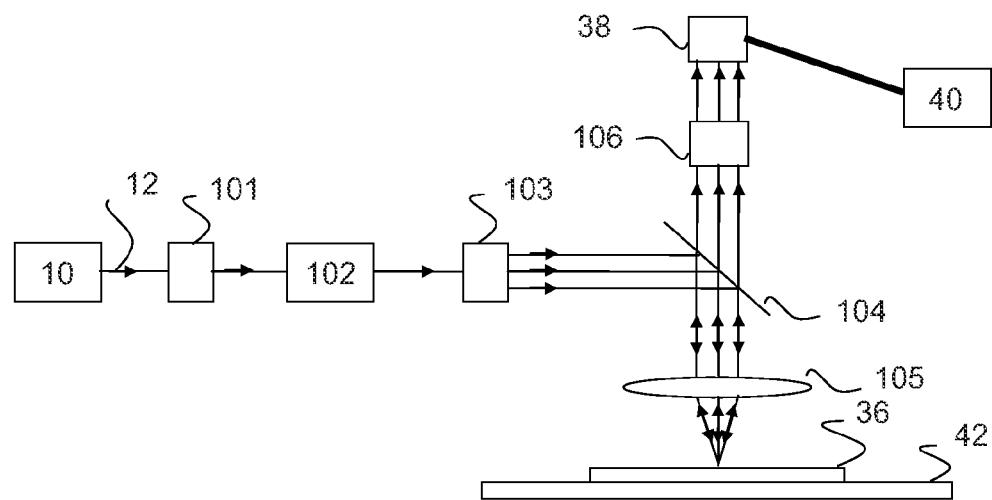

Another metrology system embodiment is illustrated in FIG. 10. The metrology system includes an illumination subsystem. As shown in FIG. 10, the illumination subsystem includes light source 10 configured to generate coherent pulses of light (shown generally in FIG. 10 by light beam 12). The light source may be further configured as described herein. The illumination subsystem also includes optics 102 configured to reduce the coherence of the light pulses from light source 10. Optics 102 include one or more dispersive elements positioned in the path of the coherent pulses of light. The one or more dispersive elements are configured to reduce coherence of the pulses of light by mixing spatial and temporal characteristics of light distribution in the pulses of light. The dispersive element(s) may be further configured as described herein. Optics 102 also include one or more electro-optic modulators positioned in the path of the pulses of light. The electro-optic modulator(s) are configured to reduce the coherence of the pulses of light by temporally modulating the light distribution in the pulses of light. The electro-optic modulator(s) may be further configured as described herein. The illumination subsystem may include optics 101 configured to direct the light from the light source towards coherence reducing optics 102. Optics 101 may include, for example, a lens, a mirror, a beam expander, or some combination thereof.

The illumination subsystem is configured to direct the pulses of light from coherence reducing optics 102 to specimen 36 positioned in the metrology system. The system may include optics 103 configured to direct or focus the light on objective 105. Optics 103 may include, for example, a lens, a mirror, a beam expander, or some combination thereof. Optics 103 may also include one or more elements for controlling or changing the polarization and/or wavelengths of the light pulses. Optics 103 may further include one or more apertures for defining the size and location of the measurement spot on specimen 36. In addition, optics 103 may include one or more apertures for controlling the range of illumination angles on specimen 36. For example, as shown in FIG. 10, the elements of the illumination subsystem may be arranged such that the pulses of light are directed to the specimen at angles of incidence near to normal incidence (e.g., within about 30 degrees of normal incidence) after reflecting from beam splitter 104 and being focused onto the specimen by objective 105. Objective 105 may include one or more refractive elements such as lenses and/or one or more reflective elements such as curved mirrors. Furthermore, the metrology system may include a control subsystem (not shown) that is configured to alter one or more parameters of the illumination subsystem (e.g., such as a position of one or more of the elements of the illumination subsystem) such that the light can be directed from the coherence reducing optics to the specimen at different angles of incidence, different wavelengths, different polarization states, or some combination thereof.

The metrology system also includes a detection subsystem configured to detect light from the specimen (e.g., reflected, scattered, diffracted light) and to generate output responsive to the detected light. For example, as shown in FIG. 10, the detection subsystem may include detector 38. The light from the specimen may be collected by objective 105 and pass through beam splitter 104 and be directed to detector 38 by optics 106. Optics 106 may include elements and/or apertures configured to select which polarization states, wavelengths, from which angles, from which specimen locations, etc. light reaches the detector. These optics may also be configured so that light falling at different locations on the detector corresponds to different angles of incidence on the specimen (i.e. the detector may lie in a pupil plane of the optical system) similar to the configurations described in U.S. Pat. No. 4,999,014 to Gold et al., U.S. Pat. No. 5,042,951 to Gold et al., U.S. Pat. No. 5,159,412 to Willenborg et al. and U.S. Pat. No. 5,181,080 to Fanton et al., which are all incorporated by reference as if fully set forth herein. The embodiments described herein allow a pulsed laser to be used in metrology systems that, heretofore, would have required a continuous-wave light source. The detector may include any suitable detector such as an imaging detector or a non-imaging detector. The measurements of the specimen being performed by the metrology system may include any suitable measurements such as scatterometry, measurements, ellipsometry measurements, and reflectometry measurements including scatterometry measurements similar to those disclosed in U.S. Pat. No. 7,248,375 to Opsal et al. and U.S. Pat. No. 7,667,841 to Opsal, which are incorporated by reference as if fully set forth herein.

In addition, the metrology system includes a processor configured to determine one or more characteristics of the specimen using the output. For example, as shown in FIG. 10, the metrology system may include processor 40. The processor may be configured as described further herein. The metrology system shown in FIG. 10 may also be further configured as described herein.

Figure 11:
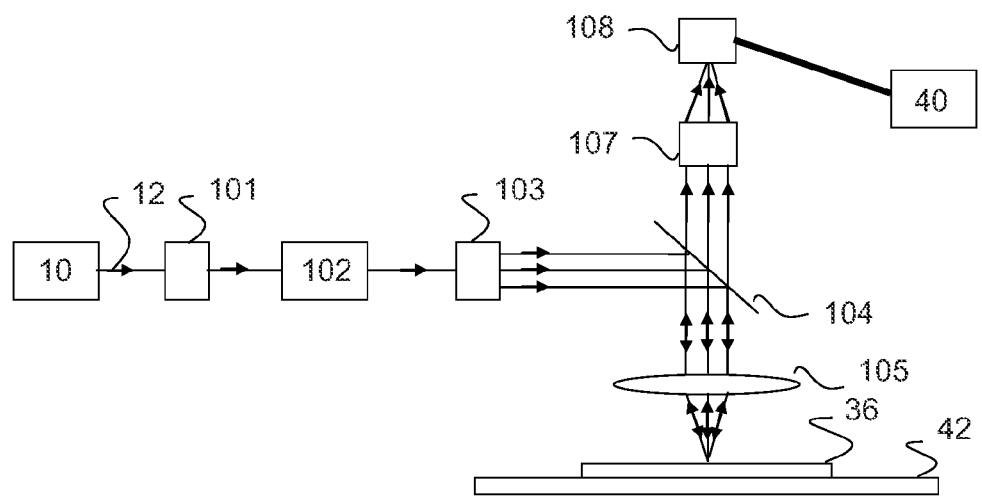
FIG. 11 is a schematic diagram illustrating a side view of one embodiment of an inspection system.

An inspection system embodiment is illustrated in FIG. 11. The inspection system includes an illumination subsystem. As shown in FIG. 11, the illumination subsystem includes light source 10 configured to generate coherent pulses of light (shown generally in FIG. 11 by light beam 12). The light source may be further configured as described herein. The illumination subsystem also includes optics 102 configured to reduce the coherence of the light pulses from light source 10. Optics 102 include one or more dispersive elements positioned in the path of the coherent pulses of light. The one or more dispersive elements are configured to reduce coherence of the pulses of light by mixing spatial and temporal characteristics of light distribution in the pulses of light. The dispersive element(s) may be further configured as described herein. Optics 102 also include one or more electro-optic modulators positioned in the path of the pulses of light exiting the dispersive element(s). The electro-optic modulator(s) are configured to reduce the coherence of the pulses of light by temporally modulating the light distribution in the pulses of light. The electro-optic modulator(s) may be further configured as described herein. The illumination subsystem may include optics 101 configured to direct the pulses of light towards coherence reducing optics 102. Optics 101 may include, for example, a lens, a mirror, a beam expander, or some combination thereof.

The illumination subsystem is configured to direct the pulses of light from coherence reducing optics 102 (e.g., from the electro-optic modulator(s)) to specimen 36 in the inspection system. The system may include optics 103 configured to direct or focus the light on objective 105. Optics 103 may include, for example, a lens, a mirror, a beam expander, or some combination thereof. Optics 103 may also include elements for controlling or changing the polarization and/or wavelengths of the light pulses. Optics 103 may further include one or more apertures for controlling the range of illumination angles at which the light is directed onto specimen 36. For example, as shown in FIG. 11, the elements of the illumination subsystem may be arranged such that the pulses of light are directed to the specimen after reflecting from beam splitter 104 and being focused onto the specimen by objective 105. Objective 105 may include one or more refractive elements such as lenses and/or one or more reflective elements such as curved mirrors. Furthermore, the inspection system may include a control subsystem (not shown) that is configured to alter one or more parameters of the illumination subsystem (e.g., such as a position of one or more of the elements of the illumination subsystem) such that the light can be directed to the specimen at different angles of incidence, different polarization states, different wavelengths, or some combination thereof.

The inspection system also includes a detection subsystem configured to detect light from the specimen and to generate output responsive to the detected light. For example, as shown in FIG. 11, the detection subsystem may include detector 108. The light from the specimen that is detected may include reflected and/or scattered light. For example, the light reflected and/or scattered from the specimen may be collected by objective 105 and pass through beam splitter 104 and be directed to detector 108 by optics 107. These optics may be configured so that light reflected and/or scattered from the specimen is imaged onto detector 108. The detector may include any suitable detector such as an imaging detector or a non-imaging detector. For example, in one embodiment, the detection subsystem is configured to detect the light by imaging the light from the specimen. In this manner, the detection subsystem may be configured as an imaging subsystem. In another embodiment, the light source is a pulsed laser light source, and the detection subsystem is configured to generate the output by image grabbing. The detection subsystem may include any suitable image grabbing detection subsystem.

In some embodiments, the light detected by the detection subsystem includes reflected light, and the inspection system is configured as a bright field inspection system. In another embodiment, the light detected by the detection subsystem includes scattered light, and the inspection system is configured as a dark field inspection system. In an additional embodiment, the inspection system is configured as a bright field and dark field inspection system. In this manner, the inspection of the specimen being performed by the inspection system may include any suitable inspection mode such as bright field, dark field, or a combination of bright field and dark field. Optics 107 may contain one or more elements and/or one or more apertures that can be used to select which polarization state(s), which wavelength(s), and from which angle(s) light from the specimen reaches the detector.

The inspection system further includes a processor configured to detect defects on the specimen using the output. For example, as shown in FIG. 11, the inspection system may include processor 40. The processor may be configured to detect defects (e.g., pattern defects, particles, and the like) on the specimen using the output in any suitable manner. For example, pattern defects and particles may be detected by comparing image(s) of one area on a wafer with image(s) of another area that should contain a substantially identical image (e.g., comparing the same region of two or more different dies on the wafer). If three or more dies are compared, then it will generally be possible to determine which region in each image is had by it being most different from the others. The images being compared for defect detection need not be from different dies. In some cases such as memory arrays or multiple cores within a single processor, the same pattern may occur more than once within the same die and multiple images of multiple instances of the same pattern may be compared for defect detection. The inspection system shown in FIG. 11 may be further configured according to any embodiments described herein.

In one embodiment, the metrology or inspection system is configured to cause continuous relative movement between the specimen and the detection subsystem during measurements or inspection of the specimen performed by the metrology or inspection system. In this manner, the metrology or inspection system may be configured to perform "on the fly" measurements or imaging of the specimen, in which the position of the specimen with respect to the detection subsystem (and possibly the illumination subsystem) of the metrology or inspection system is not fixed during measurements. In one such embodiment, the output includes an image or measurement, and the detection subsystem is configured to generate one image or measurement for each of the pulses of light from the light source. In other words, image or signal grabbing may be synchronized with the pulses of light. For example, the metrology or inspection system may include stage 42, shown in FIGS. 9-11, on which the specimen is positioned while in the metrology or inspection system. The stage may include any suitable mechanical and/or robotic assembly known in the art.

In one embodiment, the light source is a pulsed laser light source, and the system is configured to move the specimen along a serpentine path continuously with respect to the illumination and detection subsystems while measurements or inspections are being performed on the specimen. For example, the metrology or inspection system may include a control subsystem (not shown) that is configured to move the specimen along a path (e.g., a serpentine path) continuously with respect to the illumination and detection subsystems while the measurements or inspections are being performed on the specimen. In such a configuration, the illumination and detection subsystems may remain stationary while the specimen is being moved. In a similar manner, the metrology or inspection system may include a control subsystem (not shown) that is configured to move the illumination subsystem and/or detection subsystem in some manner continuously while the position of the specimen is not altered. In another configuration, both the specimen and at least some optics of the illumination and/or detection subsystems may be moved simultaneously to thereby continuously change the position of the specimen with respect to the optics of the illumination subsystem and/or detection subsystem while the measurements are being performed on the specimen. Many different control subsystems that are suitable for moving the specimen and/or at least some optics of the illumination and detection subsystems in the metrology and inspection systems described herein are known in the art and thus will not be described further.

The metrology and inspection systems described herein may be further configured according to any of the embodiments described herein. In addition, the metrology and inspection systems described herein may be used to perform any of the method embodiments described herein.

An additional embodiment relates to a method for illuminating a specimen for metrology measurements or inspection. The method includes generating coherent pulses of light. Generating the coherent pulses of light may be performed using any of the light sources described herein. The coherent pulses of light may include any of the light described herein. The method also includes reducing coherence of the pulses of light by mixing spatial and temporal characteristics of light distribution in the pulses of light. Reducing the coherence of the pulses of light by mixing spatial and temporal characteristics of the light distribution may be performed as described further herein (e.g., using a dispersive element described herein). In addition, the method includes reducing the coherence of the pulses of light by temporally modulating the light distribution in the pulses of light. Reducing the coherence of the pulses of light by temporally modulating the light distribution in the pulses of light may be performed as described further herein (e.g., using an electro-optic modulator described herein). In one embodiment, the reducing steps are performed without using mechanical devices. The method may also include further reducing the coherence of the pulses of light as described herein (e.g., using an additional dispersive element and/or a reflective element described herein). The method further includes subsequent to the reducing steps, directing the pulses of light to the specimen positioned in a metrology or inspection system. Directing the pulses of light to the specimen may be performed as described further herein. The metrology or inspection system may be further configured as described herein.

Each of the embodiments of the method described above may include any other step(s) of any method(s) described herein. In addition, each of the embodiments of the method described above may be performed by any illumination subsystem and metrology or inspection system embodiments described herein.

Further modifications and alternative embodiments of various aspects of the invention will be apparent to those skilled in the art in view of this description. For example, embodiments for illuminating a specimen for metrology measurements or inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An inspection system, comprising:
    an illumination subsystem, wherein the illumination subsystem comprises:
        a light source configured to generate coherent pulses of light;
        a dispersive element positioned in the path of the coherent pulses of light, wherein the dispersive element is configured to reduce coherence of the pulses of light by mixing spatial and temporal characteristics of light distribution in the pulses of light; and
        an electro-optic modulator positioned in the path of the pulses of light exiting the dispersive element, wherein the electro-optic modulator is configured to reduce the coherence of the pulses of light by temporally modulating the light distribution in the pulses of light, wherein the electro-optic modulator is further configured to have an amplitude that provides about $10^3$ aperiodic samples on each period thereby providing a de-coherence time of about $10^{-13}$ seconds, and wherein the illumination subsystem is configured to direct the pulses of light from the electro-optic modulator to a specimen;
    a detection subsystem configured to detect light from the specimen and to generate output responsive to the detected light; and
    a processor configured to detect defects on the specimen using the output.

2. The system of claim 1, wherein the inspection system is configured to cause continuous relative movement between the specimen and at least some optics of at least one of the illumination and detection subsystems during inspection of the specimen performed by the inspection system.

3. The system of claim 1, wherein the detection subsystem is further configured to detect the light by imaging the light from the specimen.

4. The system of claim 1, wherein the output comprises an image or measurement, and wherein the detection subsystem is further configured to generate one image or measurement for each of the pulses of light from the light source.

5. The system of claim 1, wherein the light source is a pulsed laser light source, and wherein the detection subsystem is further configured to generate the output by image grabbing.

6. The system of claim 1, wherein the light source is a pulsed laser light source, and wherein the inspection system is configured to cause continuous relative movement between the specimen and at least some optics of at least one of the illumination and detection subsystems during inspection of the specimen performed by the inspection system.

7. The system of claim 1, wherein the light source is a pulsed laser light source, and wherein the inspection system is configured to move the specimen along a serpentine path continuously with respect to the illumination and detection subsystems while inspection is being performed on the specimen.

8. The system of claim 1, wherein the electro-optic modulator has a modulation frequency of about 1 GHz to about 10 GHz.

9. The system of claim 1, wherein the electro-optic modulator is further configured to operate in a traveling wave operation mode, and wherein the electro-optic modulator has a modulation frequency of about 1 GHz to about 10 GHz.

10. The system of claim 1, wherein the light detected by the detection subsystem comprises reflected light, and wherein the inspection system is configured as a bright field inspection system.

11. The system of claim 1, wherein the light detected by the detection subsystem comprises scattered light, and wherein the inspection system is configured as a dark field inspection system.

12. The system of claim 1, wherein the inspection system is configured as a bright field and dark field inspection system.

13. The system of claim 1, wherein a duration of the pulses of light generated by the light source is less than 10 nanoseconds.

14. The system of claim 1, wherein the light source is a laser light source.

15. The system of claim 1, wherein the dispersive element is a prism.

16. The system of claim 1, wherein the dispersive element is a diffraction grating.

17. The system of claim 1, wherein the illumination subsystem further comprises an additional dispersive element positioned in the path of the pulses of light exiting the electro-optic modulator, and wherein the additional dispersive element is configured to reduce the coherence of the pulses of light by mixing the spatial and temporal characteristics of the light distribution in the pulses of light.

18. The system of claim 17, wherein the illumination subsystem is further configured to direct the pulses of light from the additional dispersive element to the specimen.

19. The system of claim 17, wherein the illumination subsystem further comprises refractive optics positioned between the electro-optic modulator and the additional dispersive element.

20. The system of claim 17, wherein the illumination subsystem further comprises a reflective element positioned in the path of the pulses of light exiting the additional dispersive element, wherein the reflective element is configured to direct the pulses of light exiting the additional dispersive element back through the additional dispersive element, the electro-optic modulator, and the dispersive element, and wherein the illumination subsystem is further configured to direct the pulses of light from the dispersive element to the specimen.

21. The system of claim 1, wherein the illumination subsystem further comprises a reflective element positioned in the path of the pulses of light exiting the electro-optic modulator, wherein the reflective element is configured to direct the pulses of light exiting the electro-optic modulator back through the electro-optic modulator and the dispersive element, and wherein the illumination subsystem is further configured to direct the pulses of light from the dispersive element to the specimen.

22. The system of claim 1, wherein the electro-optic modulator is further configured to change the temporal modulation of the light distribution in the pulses of light at tenth picosecond time intervals.

23. The system of claim 1, wherein the electro-optic modulator is further configured to operate in a traveling wave operation mode.

24. The system of claim 1, wherein the pulses of light generated by the light source comprise light having different wavelengths, and wherein the illumination subsystem is further configured to direct the light having the different wavelengths along different optical paths through the illumination subsystem.

25. The system of claim 1, wherein the illumination subsystem is not configured to reduce the coherence of the pulses of light using mechanical devices.

26. A method for illuminating a specimen for inspection, comprising:
    generating coherent pulses of light;
    reducing coherence of the pulses of light by mixing spatial and temporal characteristics of light distribution in the pulses of light;
    reducing the coherence of the pulses of light by temporally modulating the light distribution in the pulses of light with an electro-optic modulator, wherein the electro-optic modulator is configured to have an amplitude that provides about $10^3$ aperiodic samples on each period thereby providing a de-coherence time of about $10^{-13}$ seconds; and
    subsequent to the reducing steps, directing the pulses of light to the specimen positioned in an inspection system.

27. The method of claim 26, wherein the reducing steps are performed without using mechanical devices.

* * * * *